US010148439B2

(12) United States Patent
Barthe

(10) Patent No.: US 10,148,439 B2
(45) Date of Patent: Dec. 4, 2018

(54) METHODS AND SYSTEMS FOR CONTROLLING MEDICAL DEVICE USAGE

(71) Applicant: Ardent Sound, Inc., Mesa, AZ (US)

(72) Inventor: Peter G. Barthe, Phoenix, AZ (US)

(73) Assignee: ARDENT SOUND, INC., Mesa, AZ (US)

( * ) Notice: Subject to any disclaimer, the term of this patent is extended or adjusted under 35 U.S.C. 154(b) by 205 days.

(21) Appl. No.: 14/777,054

(22) PCT Filed: Mar. 17, 2014

(86) PCT No.: PCT/US2014/030822
§ 371 (c)(1),
(2) Date: Sep. 15, 2015

(87) PCT Pub. No.: WO2014/145962
PCT Pub. Date: Sep. 18, 2014

(65) Prior Publication Data
US 2016/0036590 A1 Feb. 4, 2016

Related U.S. Application Data

(60) Provisional application No. 61/800,496, filed on Mar. 15, 2013.

(51) Int. Cl.
H04L 29/00 (2006.01)
H04L 9/32 (2006.01)
H04L 9/08 (2006.01)
G06F 21/60 (2013.01)
G16H 40/40 (2018.01)

(52) U.S. Cl.
CPC .......... *H04L 9/3226* (2013.01); *G06F 21/606* (2013.01); *G16H 40/40* (2018.01); *H04L 9/0891* (2013.01); *G06F 2221/2141* (2013.01); *H04L 2209/88* (2013.01)

(58) Field of Classification Search
CPC . H04L 2209/88; G06F 21/606; G06F 19/3412
See application file for complete search history.

(56) References Cited

U.S. PATENT DOCUMENTS

| 7,039,810 B1 | 5/2006 | Nichols |
| 2004/0186746 A1 | 9/2004 | Angst et al. |
| 2008/0140160 A1* | 6/2008 | Goetz ............... A61N 1/37288 607/60 |

(Continued)

OTHER PUBLICATIONS

The International Search Report and Written Opinion as dated Nov. 19, 2014 for International Application No. PCT/US2014/030822.

*Primary Examiner* — Ellen Tran
(74) *Attorney, Agent, or Firm* — Quarles & Brady LLP

(57) ABSTRACT

Various embodiments provide systems and methods for securely transferring data from a secured site to a medical device. Some embodiments provide systems and methods for securely uploading data from a medical device to a secured site. In some embodiments described herein, data can be downloaded from a secured site to a key and after severing communication with the secured site, key can be coupled to a device and download the data to the device, in some embodiments, a public and private key pair may be used to securely download data to a device.

20 Claims, 12 Drawing Sheets

(56) References Cited

U.S. PATENT DOCUMENTS

| | | |
|---|---|---|
| 2009/0125084 A1 | 5/2009 | Juels et al. |
| 2009/0249076 A1 | 10/2009 | Reed et al. |
| 2010/0131084 A1 | 5/2010 | Van Camp |
| 2010/0292556 A1* | 11/2010 | Golden ................ A61B 5/7465 600/364 |
| 2011/0112696 A1* | 5/2011 | Yodfat ................ G06F 19/3412 700/283 |
| 2011/0258333 A1 | 10/2011 | Pmerantz et al. |
| 2012/0179908 A1 | 7/2012 | Duma |

\* cited by examiner

METHODS AND SYSTEMS FOR CONTROLLING MEDICAL DEVICE USAGE

CROSS-REFERENCE TO RELATED APPLICATIONS

This application represents the national stage entry of PCT International Application No. PCT/US2014/030822 filed on Mar. 17, 2014 and claims priority to and the benefit of U.S. Provisional Patent Application Ser. No. 61/800,496, filed Mar. 15, 2013, the entire contents of which are incorporated by reference herein.

BACKGROUND

As computerization of medical devices becomes commonplace, such devices may be designed to be interfaced onto a computer network. A networked medical device may allow the device to communicate with a database on the network to transfer data or to upload patient information. However, a networked device can be corrupted via viruses, worms, root-kits, remote access, denial of service, and other malware and attacks, which is important for medical devices. In addition, a non-networked device is simplified and less prone to obsolescence as network technologies and settings change. Regulatory agencies may require a threat analysis and additional testing of a networked medical device.

In some cases, a personal key can authenticate a user of a computer and then authentication and encryption hardware/firmware, which may be resident on the key, can allow certain usage of hardware and/or software by the computer. In some instances, such usage may be debited or checked from the key before, during, and/or after the certain usage by the computer is attempted, in process, or completed. The key can protect the operating software on the computer to various degrees against hacker attempts to change it, with the key.

SUMMARY

Various embodiments provide systems and methods for controlling medical device usage. Some embodiments provide limits of use for a disposable component coupled to a device. For example, a limit of use for disposable component can be a number of treatments that can be performed with the disposable component. Another sample a limit of use for disposable component can be a particular treatment that the device can perform while coupled to disposable component.

Various embodiments provide systems and methods for securely transferring data from a secured site to a medical device. Some embodiments provide systems and methods for securely uploading data from a medical device to a secured site. In some embodiments described herein, data can be downloaded from a secured site to a key and after severing communication with the secured site, key can be coupled to a device and download the data to the device. In some embodiments, a public and private key pair may be used to securely download data to a device.

Accordingly, various embodiments provide methods for using a component coupled to a medical device. In some embodiments, a method can include the steps of interfacing a communication key with a computer cloud; downloading encrypted authorization codes from the cloud onto key; severing communication between the cloud and the key; interfacing the key with a device controller in communication with a medical device; coupling a component to the medical device; downloading the authorization codes to at least one of the medical device and the component; and initiating the component for use when coupled to the medical device.

Various embodiments provide a treatment system. In some embodiments, the system can include a secured key comprising encrypted protected memory; a secured site located on a computing cloud and configured to securely communicate with the secured key; an interface configured for secured communication between the secured site and the secured key; a treatment device; a device controller in communication with and configured to control the treatment device, the device controller comprising a communication port configured for communication with the secured key; and a component coupled to the treatment device and in communication with the secured key.

Various embodiments provide methods of enabling a treatment device. In some embodiments, a method can include the steps of downloading an authorization code from a cloud computing network on to a secured electronic key; interfacing the secured electronic key with component treatment module coupled to a treatment device; initiating communication between the secured electronic key and the component treatment module; determining if the component treatment module is enabled to be authorized by the secured electronic key; downloading the authorization code to the component treatment module; authorizing the component treatment module with the authorization code; and enabling operation of the treatment device coupled to the component treatment module, which has been authorized.

DRAWINGS

The present disclosure will become more fully understood from the specification, and the accompanying drawings, wherein.

Figure 1:
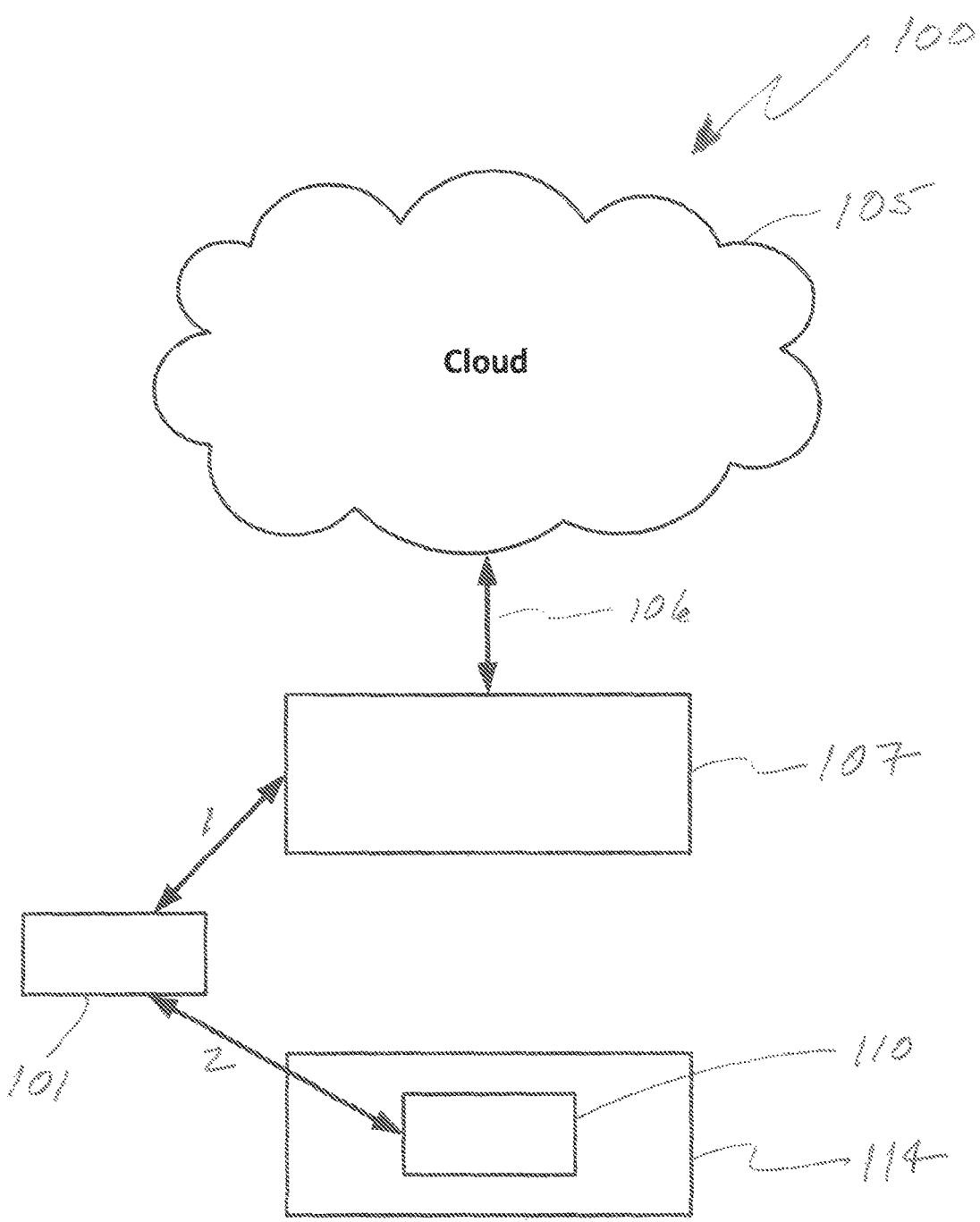
FIG. 1 is a diagram illustrating a system, in accordance with various embodiments.

The drawings described herein are for illustrative purposes only of selected embodiments and not all possible implementations, and are not intended to the scope of any of the exemplary embodiments disclosed herein or any equivalents thereof. It is understood that the drawings are not

DESCRIPTION

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic tissue treatment, as described herein, are merely indicative of exemplary applications for the invention. For example, the principles, features and methods discussed may be applied to any medical application.

Various embodiments provide systems and methods for controlling medical device usage. Some embodiments provide limits of use for a disposable component coupled to a device. For example, a limit of use for disposable component can be a number of treatments that can be performed with the disposable component. In another example, a limit of use for disposable component can be a particular treatment that the device can perform while coupled to disposable component.

Various embodiments provide systems and methods for securely transferring data from a secured site to a medical device. Some embodiments provide systems and methods for securely uploading data from a medical device to a secured site. In some embodiments described herein, data can be downloaded from a secured site to a key and after severing communication with the secured site, key can be coupled to a device and download the data to the device. In some embodiments, a public and private key pair may be used to securely download data to a device.

In various embodiments, data can be any type of data that can be downloaded from a secured site to a device. The data can be a data packet that is downloadable from the secured site to the device. For example, data can allow and/or limit usage of the device, such as for example, a medical device. In another example, data can be a device upgrade, for example, a software upgrade, or a new software module or a new version of software. For example, data can be a new method, such as for example a new treatment method for medical device. In another example data can be an activation of option, when the option resides on the device but is dormant.

In another example, data can be a lifetime, of a particular component. A lifetime can be a number of treatments that can be performed with the disposable component. A lifetime of a particular component can be for example a prescribed number of lines available for an emission source. For example, an emission source can be at least one of an ultrasound transducer, a RF generator, and a laser. In one example, an emission source is an ultrasound transducer.

Various embodiments provide a treatment system. In some embodiments, the system can include a secured key comprising encrypted protected memory; a secured site located on a computing cloud and configured to securely communicate with the secured key; an interface configured for secured communication between the secured site and the secured key; a treatment device, a device controller in communication with and configured to control the treatment device, the device controller comprising a communication port configured for communication with the secured key; and a component coupled to the treatment device and in communication with the secured key.

In some embodiments, the system can include a processor configured to communicate with the secured site and comprising a communication port configured for communication with the secured key. In some embodiments, the treatment device is an ultrasound treatment device. In some embodiments, the component is an ultrasound transducer module. In some embodiments, the component comprises an EEPROM configured to communicate with the secured key and comprising an authorization protocol.

In some embodiments, the system can include an authorization code configured to be downloaded from the secured site onto the secured key and further configured to be transmitted from the secured key to the EEPROM. In some embodiments, the authorization code is configured to be delivered to the authorization protocol and permit the authorization protocol to enable operation of the component. In some embodiments, the system can include a treatment counter embedded into the secured key and in communication with the component.

In some embodiments, the system can include an expiration function configured to execute after a predetermined number of treatments as clocked by the treatment counter and configured disable operation of the component upon completion of the predetermined number of treatments. In some embodiments, the treatment device, the device controller and the communication port are enclosed into one unit.

In some embodiments, the system can include an interface sever module configured to sever the interface between the secured server and the secured key and configured to automatically sever the interface upon communication of the device controller with the secured key. In some embodiments, the system can include a software update configured to be delivered from the secured site to the secured key and further configured to be uploaded from the secured key to the device controller and configured to update the software rev on running the device controller. In some embodiments, the system can include a firewall configured to automatically operate upon operation of the component and configured to prevent any communication to the device controller with the cloud.

Now with reference to FIG. 1, a diagram illustrating a system is presented in accordance with various embodiments. System 100 comprises a key 101 which can be configured to interface with a processor 107 as well as, with a controller 110. Processor 107 communicates with cloud 105 through an interface 106. Controller 110 communicates with a device 114. In some embodiments, device 114 comprises controller 110. In some embodiments, device 114 comprises memory, which is in communication with controller 110. Controller 110 communicates with and controls device 114.

In various embodiments, cloud 105 can be any system or network that enables processor 107 to communicate with a control site which may be a webpage or may be located on a secure server. In some embodiments, cloud 105 can be the Internet. For example, cloud 105 enables processor 107 to communicate via interface 106 with a secured website. In some embodiments, processor 107 can communicate with cloud. 105 using a web browser. In some embodiments, processor 107 can communicate with cloud 105 using an app, which may be installed on processor 107.

Processor 107 can be a computer, such as, for example a desktop, a lap top, or notebook. In some embodiments, processor 107 can be a computer configured with the wired port for use as interface 106 for communication with cloud 105. In some embodiments, processor 107 can be a computer configured with a wireless port for use as interface 106 for communication with the cloud 105. In some embodiments, processor 107 can be a computer configured with both a wired port and a wireless port, either or both being configured for use as interface 106 for communication with the cloud 105. In some embodiments, processor 107 can be a smart device, such as for example, a tablet, a smart phone, an iPhone, an iPad, or a PDA. Interface 106 can be based on an Ethernet system, a wireless system, a LAN, a WAN, a cellular system, a radio system, or combinations thereof.

Processor 107 can be any device which can communicate with cloud 105 and comprises a port which can allow key 101 to communicate with processor 107, which can allow cloud 105 to communicate with key 101. In some embodiments, processor 107 comprises a port which is a USB interface to which key 101 is configured to couple to such a port. In some embodiments, processor 107 comprises a port which physically and electronically couples with key 101. In some embodiments, processor 107 comprises a wireless port which communicates wirelessly with key 101. In some embodiments, the port is configured to communicate with key 101 and allow key 101 to couple to processor 107.

Various embodiments provide methods for employing key 101 for use with device 114. Some embodiments provide methods for controlling usage of device 114. In some embodiments, device 114 can be a medical device. Processor 107 can be connected with cloud 105 via interface 106, which allows communication with the secured website hosted in cloud 105. After security authorization is recognized by the website, key 101 is interfaced with processor 107 (as indicated by arrow "1"). Processor 107 can facilitate a data upload from key 101 to the website. Processor 107 can facilitate a data download from the website onto key 101. For example, processor 107 can provide data, to website and this data can be used to determine if device 110 is valid. After website has gone through a process to determine the validity of device 114, website sends authorization codes through processor 107 to key 101. After authorization codes have been received and confirmed by key 101, the interface between key 101 and processor 107 is severed. In some embodiments, after authorization codes have been received and confirmed by key 101, the interface between key 101 and cloud 105 is severed. Although the interface between key 101 and processor 107 is severed, processor 107 may still be in communication with cloud 105 via interface 106.

Since interface between key 101 and processor 107 has been severed, key 101 can be interfaced with controller 110 (as indicated by arrow labeled "2"). In various embodiments, key 101 can be used to authenticate device 114. In some embodiments, controller 110 comprises a port that is equivalent to the port of processor 107. In some embodiments, controller comprises a wireless port configured to be in communication with key 101. Although port of controller 110 may not be equivalent on to port of processor 107, port of controller 110 is configured to allow key 101 to be in communication with device 114. In some embodiments, controller 110 is configured to allow key 101 to be in communication with device 114. Controller 110 can facilitate a data upload from key 101 to the device 114. Controller Can facilitate a data download from the device 114 onto key 101.

Figure 2:
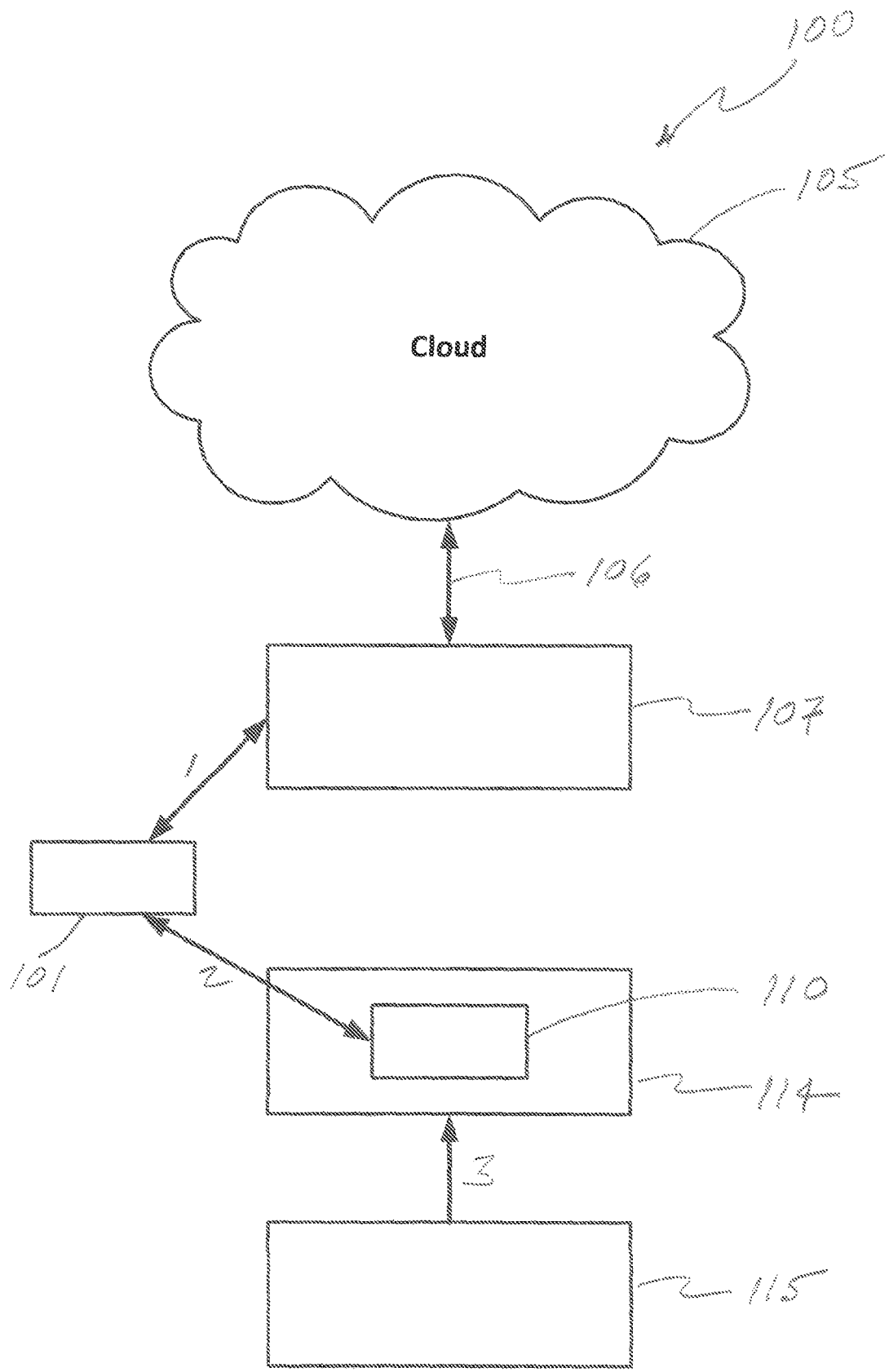
FIG. 2 is a diagram illustrating a system, in accordance with some embodiments.

Now with reference to FIG. 2, a diagram illustrating a system is presented in accordance with various embodiments. System 190 comprises key 101 which can be configured to interface with processor 107 as well as, with controller 110. Processor 107 communicates with cloud 105 through an interface 106. Device 114 comprises controller 110. In various embodiments, device 114 comprises a component 115, which can be coupled to and uncoupled from device 114. Controller 110 communicates with and controls both device 114 and component 115. In some embodiments, device 114 comprises memory, which is in communication with controller 110.

Various embodiments provide methods for employing key 101 for use with device 114 and component 115. Processor 107 can be connected with cloud 105 via interface 106, which allows communication with a website hosted in cloud 105. After security authorization is recognized by the website, key 101 is interfaced with processor 107 (as indicated by arrow "1"). Processor 107 can facilitate a data upload from key 101 to the website. Processor 107 can facilitate a data download from the website onto key 101. After data has been uploaded onto key 101, the interface between key 101 and processor 107 is severed.

Since interface between key 101 and processor 107 has been severed, key 101 can be interfaced with controller 110 (as indicated by arrow labeled "2"). In various embodiments, key 101 can be used to download data onto device 114 and/or component 115. For example, key 101 can be used to authenticate component 115. In another example, key 101 can be used to authenticate both device 114 and component 115. It some embodiments, controller 110 is configured to allow key 101 to be in communication with component 115. In some embodiments, controller 110 is configured to allow key 101 to be in communication with both device 114 and component 115.

In various embodiments, component 115 is coupled to device 114 (as indicated by arrow "3"). In some embodiments, key 101 contains data configured to enable component 115 for operation, key 101 is coupled to the controller 110, which is enabled for communication with at least one of device 114 and component 115. When device 114 is operated, key 101 provides data, such as for example, authorization codes, to allow component 115 to function when coupled to device 114. In various embodiments, controller 110 facilitates a data upload from component 115.

Figure 3:
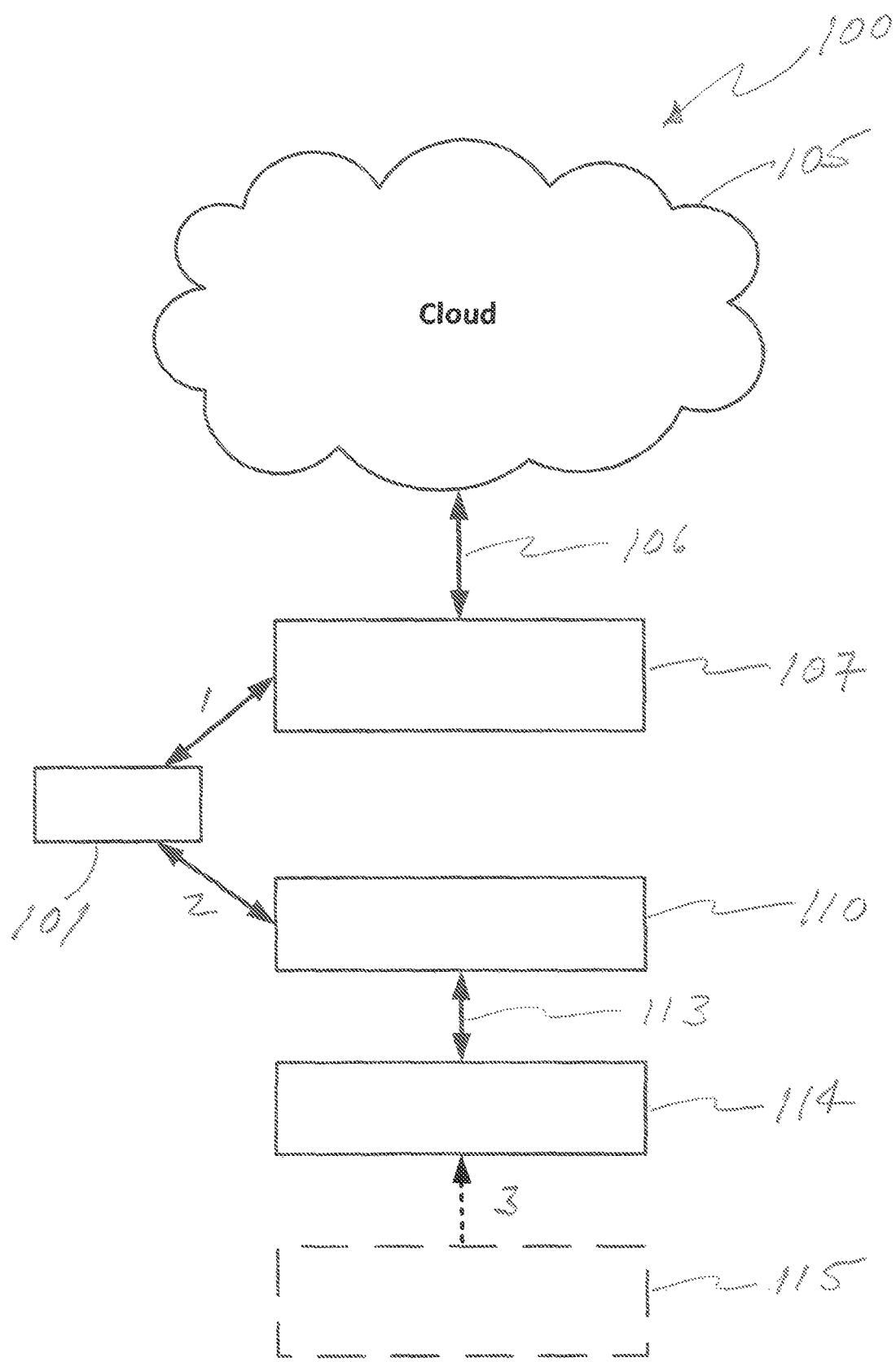
FIG. 3 is a diagram illustrating a system, in accordance with some embodiments.

Now with reference to FIG. 3, a diagram illustrating a system is presented in accordance with various embodiments. System 100 comprises a key 101 which can be configured to interface with a processor 107 as well as, with a controller 110. Processor 107 communicates with cloud 105 through an interface 106. Controller 110 communicates with a device 114 through a device interface 113. In some embodiments, controller 110 communicates with and controls device 114. In various embodiments, device 114 comprises a component 115, which can be coupled to and uncoupled from device 114. In some embodiments, controller 110 communicates with and controls both device 114 and component 115. In some embodiments, device 114 comprises memory, which is in communication with controller 110.

In various embodiments, component 115 is coupled to device 114 (as indicated by arrow "3"). In some embodiments, key 101 contains data configured to enable component 115 for operation, key 101 is coupled to the controller 110, which is enabled for communication with at least one of device 114 and component 115. When device 114 is operated, key 101 provides data, such as for example, authorization codes, to allow component 115 to function when coupled to device 114. In various embodiments, controller 110 facilitates a data upload from component 115. In one example, key 101 uploads data that tracks the use of component 115. In one example, component 115 has a prescribed lifetime, which is based on a number of treatments and such predetermined number of treatments can be downloaded as data to key 101 from the website. Upon an expiration of the lifetime of the component 115 key 101 terminates activation of the data, such as, for example, authorization codes, which was sent to device 114 and/or component 115, thus making device 114 inoperable.

In one example, upon an expiration of the lifetime of the component, key 101 invalidates the data that was sent to component 115, thus making component 115 inoperable. In one example, upon an expiration of the lifetime of the component 115, key 101 removes the data that was sent to device 114, thus making at least one of device 114 and component 115 inoperable. In an example, upon an expiration, of the lifetime of the component 114, key 101 terminates data being sent to component 115, thus making component 115 inoperable. In an example, upon an expiration of the finite lifetime of the component, key 101 invalidates data, such as, for example, authorization codes, sent to both device 114 and component 115, thus making device 114 and component 115 inoperable. In one example, interface between key 101 and controller 110 is can be severed and key 101 is then interfaced with cloud 115, to download data to key 101, such as, for example, additional lifetime and the corresponding new authorization codes, which can be downloaded to at least one of the device 114 and component 115.

Now with reference to FIG. 3, a diagram illustrating a system is presented in accordance with various embodiments. System 100 comprises key 101 which can be configured to interface with processor 107 as well as, with controller 110. Processor 107 communicates with cloud 105 through an interface 106. Controller 110 communicates with a device 114 through a device interface 113. In some embodiments, controller 110 communicates with and controls device 114. In various embodiments, device 114 comprises a component 115, which can be coupled to and uncoupled from device 114. In some embodiments, controller 110 communicates with and controls both device 114 and component 115. In some embodiments, device 114 comprises memory, which is in communication with controller 110.

Figure 4:
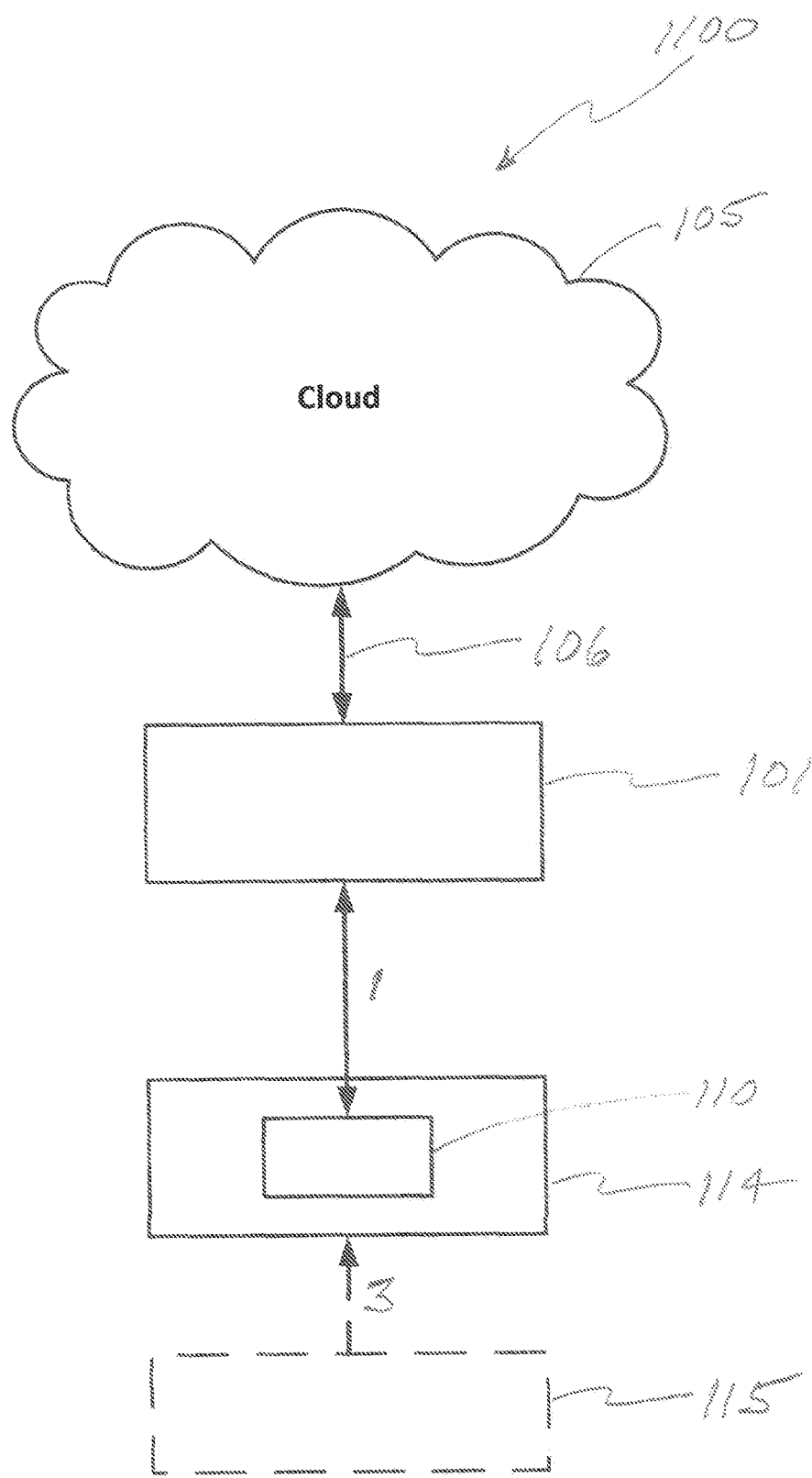
FIG. 4 is a diagram illustrating a system, in accordance with some embodiments.

Moving to FIG. 4, a diagram illustrating a system is presented in accordance with various embodiments. System 1100 comprises key 101 which can interface with cloud 105 through an interface 106, as well as, with controller 110. Device 114 comprises controller 110. In some embodiments, controller 110 communicates with and controls device 114. In various embodiments, device 114 comprises a component 115, which can be coupled to and uncoupled from device 114. In some embodiments, controller 110 communicates with and controls both device 114 and component 115. In some embodiments, device 114 comprises memory, which is in communication with controller 110.

In various embodiments, cloud 105 can be any system or network that enables key 101 to communicate with a control site which may be a webpage or may be located on a secure server. In some embodiments, cloud 105 can be the Internet. For example, cloud 105 enables key 101 to communicate via interface 106 with a secured website. In some embodiments, key 101 can communicate with cloud 105 using a web browser. In some embodiments, key 101 can communicate with cloud 105 using an app, which may be installed on key 101.

Various embodiments provide methods for employing key 101 for use with device 114. Key 101 can be connected with cloud 105 via interface 106, which allows communication with a website hosted in cloud 105. In some embodiments, website goes through a process to determine the validity of component 115, and website then sends data to key 101."). Interface 106 can facilitate a data upload from key 101 to the website. Interface 106 can facilitate a data download from the website onto key 101. After data has been uploaded onto key 101, the interface between key 101 and processor 107 is severed. After data has been received and confirmed by key 101, the interface between key 101 and cloud 105 is severed.

Since interface between key 101 and cloud 105 has been severed, key 101 can be interfaced with controller 110 (as indicated by arrow labeled "1"). In various embodiments, key 101 can be used to authenticate device 114 and/or component 115. In various embodiments, key 101 can be used to authenticate component 115. In various embodiments, key 101 can be used to authenticate device 114. In various embodiments, key 101 can be used to authenticate both device 114 and component 115. In some embodiments, controller comprises a wireless port configured to be in communication with key 101. Although port of controller 110 may not be equivalent on to port of processor 107, port of controller 110 is configured to allow key 101 to be in communication with device 114 and/or component 115. In some embodiments, controller 110 is configured to allow key 101 to be in communication with device 114. In some embodiments, controller 110 is configured to allow key 101 to be in communication with component 115. In some embodiments, controller 110 is configured to allow key 101 to be in communication with both device 114 and component 115.

In various embodiments, component 115 is coupled to device 114 (as indicated by arrow "3"). In some embodiments, key 101 contains data configured to enable component 115 for operation, key 101 is coupled to the controller 110, which is enabled for communication with at least one of device 114 and component 115. When device 114 is operated, key 101 provides data, such as for example, authorization codes, to allow component 115 to function when coupled to device 114. In various embodiments, controller 110 facilitates a data upload from component 115. In one example, key 101 uploads data that tracks the use of component 115. In one example, component 115 has a prescribed lifetime, which is based on a number of treatments and such predetermined number of treatments can be downloaded as data to key 101 from the website. Upon an expiration of the lifetime of the component 115, key 101 terminates activation of the data, such as, for example, authorization codes, which was sent to device 114 and/or component 115, thus making device 114 inoperable. Is one example, upon an expiration of the lifetime of the component, key 101 invalidates the data that was sent to component 115, thus making component 113 inoperable. In one example, upon an expiration of the lifetime of the component 115, key 101 removes the data that was sent to device 114, thus making at least one of device 114 and component 115 inoperable. In an example, upon an expiration of the lifetime of the component 114, key 101 terminates data being sent to component 115, thus making component 115 inoperable. In an example, upon an expiration of the finite lifetime of the component, key 101 invalidates data, such as, for example, authorization codes, sent to both device 114 and component 115, thus making device 114 and component 115 inoperable. In one example, interface between key 101 and controller 110 is can be severed and key 101 is then interfaced with cloud 115, to download data to key 101, such as, for example, additional lifetime and the corresponding new authorization codes, which can be downloaded to at least one of the device 114 and component 115.

Figure 5:
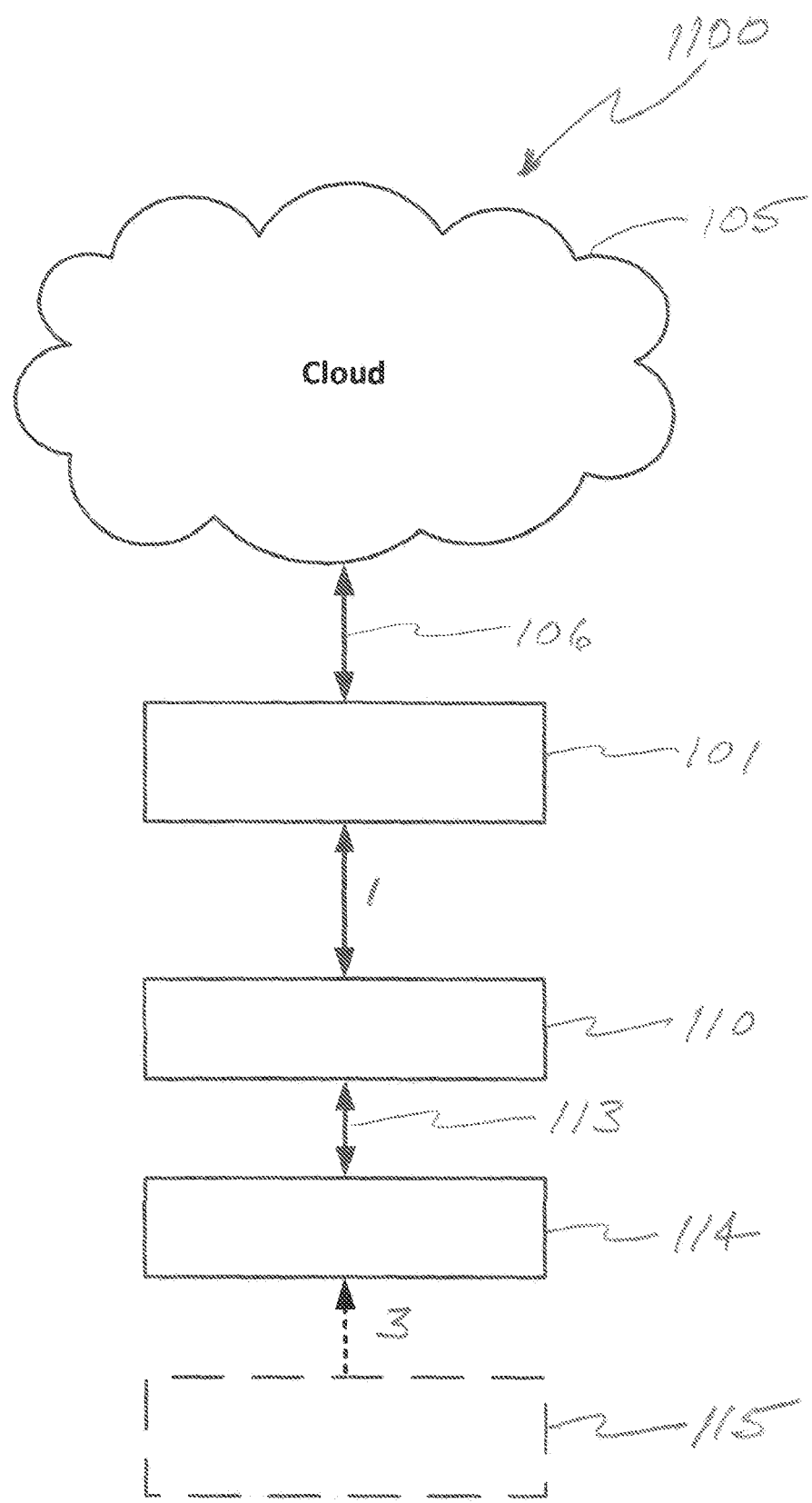
FIG. 5 is a diagram illustrating a system, in accordance with some embodiments.

Moving to FIG. 5, a diagram illustrating a system is presented in accordance with various embodiments. System 1100 comprises key 101 which could interface with cloud 105 through an interface 106, as well as, with controller 110. Controller 110 communicates with device 114 through a device interface 113. In some embodiments, controller 110 communicates with and controls device 114. In various embodiments, device 114 comprises a component 115, which can be coupled to and uncoupled from device 114. In some embodiments, controller 140 communicates with and controls both device 114 and component 115. In some embodiments, device 114 comprises memory, which is in communication with controller 110.

Figure 6:
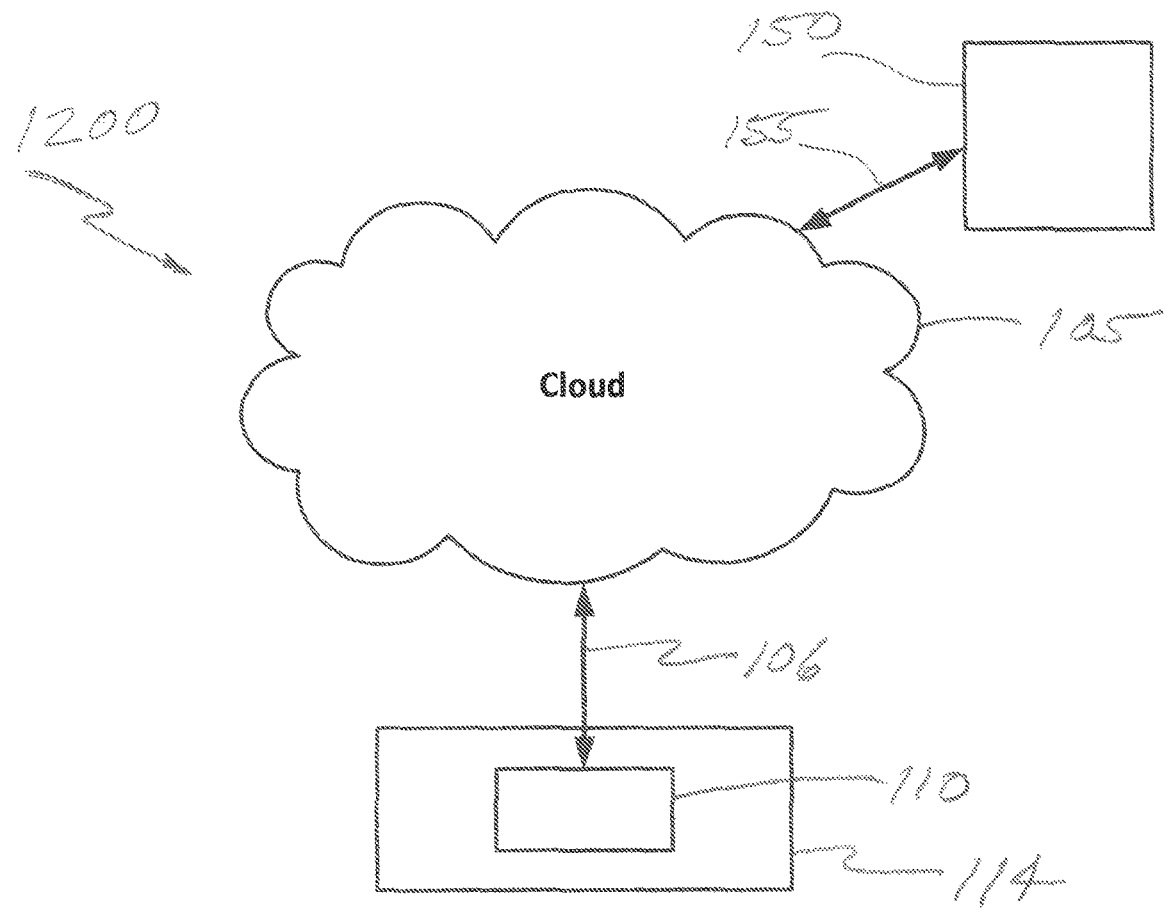
FIG. 6 is a diagram illustrating a system, in accordance with some embodiments.

Turning to FIG. 6, a diagram illustrating a system is presented in accordance with various embodiments. System 1200 comprises controller 110, which can interface with cloud 105 through an interface 106. Device 114 comprises controller 110. In some embodiments, controller 110 communicates with and controls device 114. In some embodiments, device 114 comprises memory, which is in communication with controller 110. In some embodiments, secured site 150 can include a secured interface 155 through cloud 105. For example, secured interface 155 can be a VPN.

Figure 7:
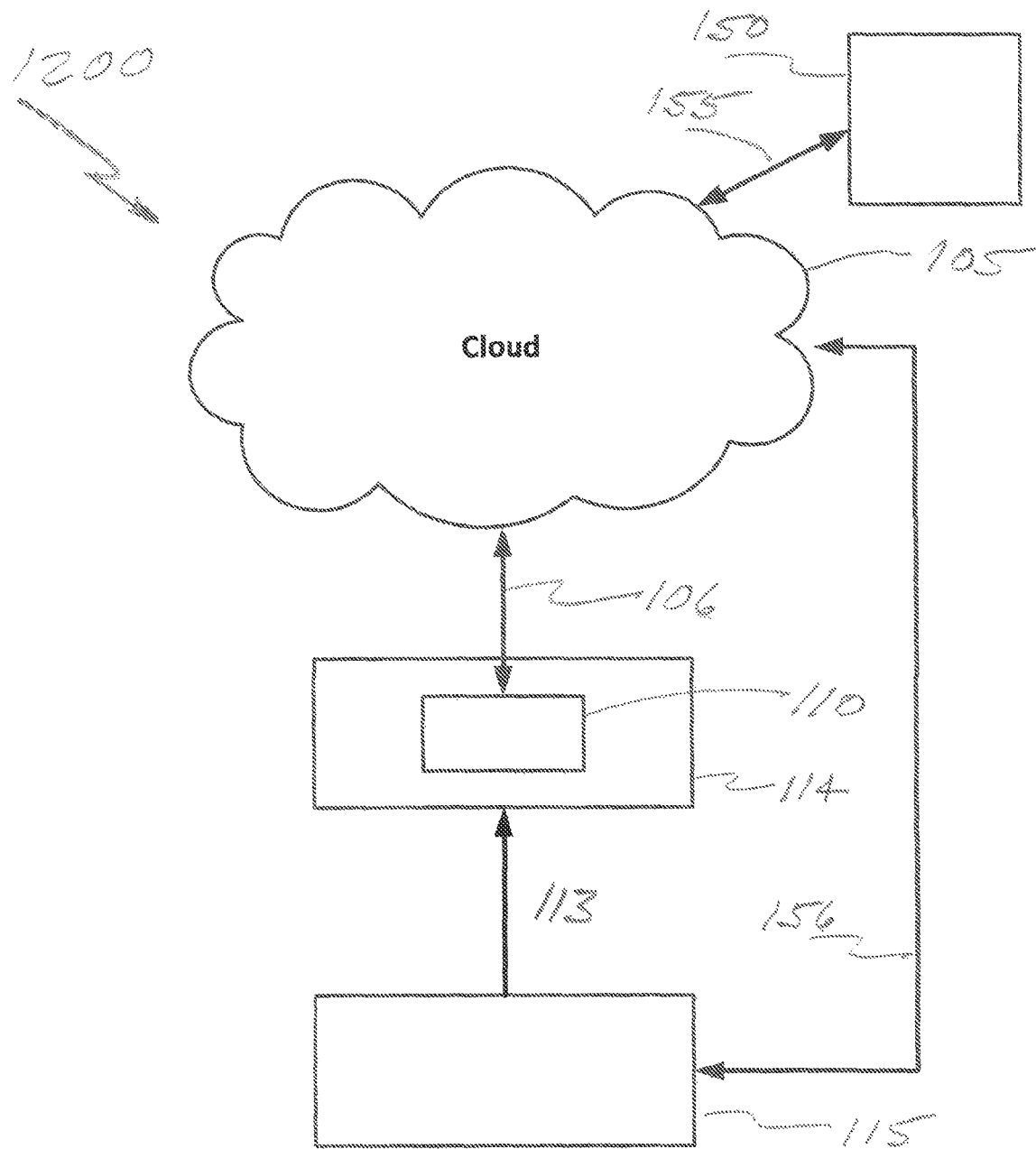
FIG. 7 is a diagram illustrating a system, in accordance with some embodiments.

In FIG. 7, a diagram illustrating a system is presented. In accordance with various embodiments. System 1200 comprises controller 110, which could interface with cloud 105 though interface 106. Controller 110 communicates with device 114 through a device interface 113. In some embodiments, controller 110 communicates with and controls device 114. In various embodiments, device 114 comprises component 115, which can be coupled to and uncoupled from device 114. In some embodiments, controller 110 communicates with and controls both device 114 and component 115. In some embodiments, component 115 communicates with cloud 105 though interface 156. In some embodiments, secured site 150 can include a secured interface 155 through cloud 105. For example, secured interface 155 can be a VPN.

With reference back to FIGS. 1-5, various embodiments provide methods for employing key 101 for use with device 114. Some embodiments provide methods for controlling usage of device 114. In some embodiments, device 114 can be a medical device. Processor 107 can be connected with cloud 105 via interface 106, which allows communication with a website hosted in cloud 105. After security authorization is recognized by the website, key 101 is interfaced with processor 107 (as indicated by arrow "1"). Processor 107 can provide data to website and this data can be used to determine if component 115 is valid. After website has gone through a process to determine the validity of component 115, website sends authorization codes through processor 107 to key 101. After authorization codes have been received and confirmed by key 101, the interface between key 101 and processor 107 is severed. In some embodiments, after authorization codes have been received and confirmed by key 101, the interface between key 101 and cloud 105 is severed. Although the interface between key 101 and processor 107 is severed, processor 107 may still be in communication with cloud 105 via interface 106.

Various embodiments provide methods for using a component coupled to a medical device. In some embodiments, a method can include the steps of interfacing communication key with a computer cloud; downloading encrypted authorization codes from the cloud onto key; severing communication between the cloud and the key; interfacing the key with a device controller in communication with a medical device; coupling a component to the medical device; downloading the authorization codes to at least one of the medical device and the component; and initiating the component for use when coupled to the medical device.

In some embodiments, a method can include the step of determining if the component is valid. In some embodiments, a method can include the step of operating the medical device and the component.

In some embodiments, the method can include the step of counting a number of treatments performed by the component during the operating the medical device and the component. In some embodiments, the method can include the step of providing a limit of the number of treatments performed by the component during the operating the medical device and the component. In some embodiments, the method can include the step of disabling the component upon reaching the limit of the number of treatments performed by the component during the operating the medical device and the component.

In some embodiments, the authorization codes enable operation of the component. In some embodiments, the method can include the step of reviewing a current version of software on the controller. In some embodiments, the method can include the step of determining if a software update is available on the key. In some embodiments, the method can include the step of downloading the software update to the controller and updating the current software with the software update.

Various embodiments provide methods of enabling a treatment device. In some embodiments, a method can include the steps of downloading an authorization code from a cloud computing network on to a secured electronic key; interfacing the secured electronic key with component treatment module coupled to a treatment device; initiating communication between the secured electronic key and the component treatment module; determining if the component treatment module is enabled to be authorized by the seemed electronic key; downloading the authorization code to the component treatment module; authorizing the component treatment module with the authorization code; and enabling operation of the treatment device coupled to the component treatment module, which has been authorized.

In some embodiments, a method can include the steps of disabling the component treatment module, if the component treatment module is not enabled to be authorized by the secured electronic key; and preventing operation of the treatment device coupled to the component treatment module, which has been disabled.

In some embodiments, a method can include operating the treatment device coupled to the component treatment module, which has been authorized. In some embodiments, a method can include counting on the secured electronic key a number of treatments performed by the component treatment module during the operating the treatment device coupled to the component treatment module, which has been authorized. In some embodiments, a method can include providing on the secured electronic key a limit of the number of treatments performed by the component treatment module during the operating the treatment device coupled to the component treatment module, which has been authorized. In some embodiments, a method can include disabling the component treatment module upon reaching the limit of the number of treatments performed by the component during the operating the treatment device coupled to the component treatment module, which has been authorized.

In some embodiments, a method can include establishing a communication interface between the secured electronic key and the cloud computing network before the step of downloading the authorization code from the cloud computing network on to the secured electronic key. In some embodiments, a method can include severing the communication interface between the secured electronic, key and the cloud computing network after the step of downloading the authorization code from the cloud computing network on to the secured electronic key.

In some embodiments, a method can include the steps of downloading a software update from the cloud computing network onto the secured electronic key; notifying the treatment device of the software update upon the step of the initiating communication between the secured electronic key and the component treatment module; downloading the software update from the secured electronic key to the cot device; and initiating the software update on the treatment device.

In some embodiments, a method can include preventing the secured electronic key from interfacing with the cloud computing network upon the step of the initiating communication between the secured electronic key and the component treatment module. In some embodiments, a method can include delivering the authorization code to the secured electronic key from an attachment to an email message. In some embodiments, the treatment device and the secured electronic key integrated together into a single device.

EXAMPLES

Figure 8:
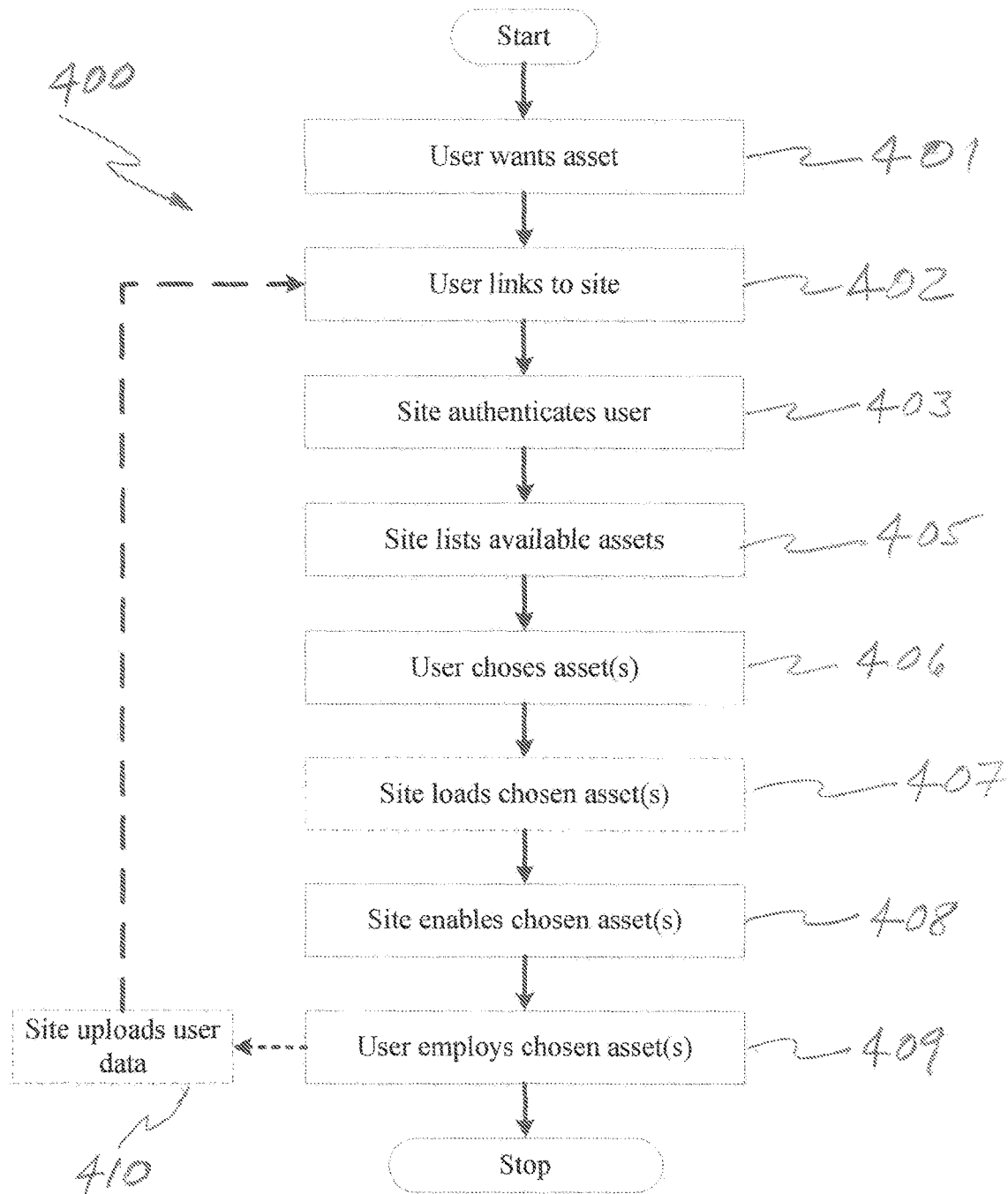
FIG. 8 is a flowchart illustrating methods, in accordance with some embodiments.

Moving to FIG. 8, a flowchart illustrating operation of the system is provided, according to various embodiments. According to various methods, a user wants to acquire asset(s) (step 401), which is configured for link, to secured site (step 402). In one example, link to site 402 can be a user coupling key 101 to processor 107. In another example, the secured site may be located at factory or at a vendor or distributor location.

In various embodiments, asset(s) can be any type of data that can be transferred from a secured site to the user. Asset(s) a data packet that is downloadable from the secured site to the user. For example, asset can be allowed usage of the device, such as for example, a medical device. In another example, asset can be a system upgrade, for example, a software upgrade, or a new software module or a new version of software. For example, asset can be a new method, such as for example a new treatment method for medical device. In another example asset can be an activation of assistant option, when the option resides on the device but is dormant. In another example, asset can be a lifetime of a particular component. A lifetime of a particular component can be for example a prescribed number of lines available for an emission source. For example, an emission source can be at least one of an ultrasound transducer, a RE generator, and a laser. In one example, an emission source is an ultrasound transducer.

Once link to site 402 has been completed, site authenticates user (step 403). In one example, site authenticates user (step 403) can be a server at a secure site reads key 101. After site authenticates user (step 403), a set of assets are listed (step 405). In one example, a set of assets are listed (step 405) can be the server and the secure site returns a listing of assets that can be read on a display of processor 107. In the next step, user enters chosen assets (step 406) and optionally secured site loads chosen assets (step 407). In one example, user enters chosen assets (step 406) can be a user entering a selection of assets into processor 107. In one example, secured site loads chosen assets (step 407) can be the secured site downloading data to key 101 via processor 107. The methods continue with site enables chosen assets (step 408). In one example, the chosen assets may reside on key 101 and secured site downloads authentication codes to key 101, which allow chosen assets to be operational and access to the chosen assets given the user. Finally, user employs asset (step 409).

Optional step can be upload user data to secured site (step 410). For example, user data can be user logs generated by the device, which employs at least one of the chosen assets. In one example, user data can be diagnostic information useful in troubleshooting the device, which employs at least one of the chosen assets. One example, user data can be device usage information. In some embodiments, user data can be any information that can be downloaded from the users device to the secured site. In some embodiments, user data is downloaded to key 101 which is coupled to users device, then key 101 can download user data to secured site. One example, key 101 which contains downloaded user data, can be coupled to processor 107, which can facilitate an interface between key 101 and the secured site, in order to, transfer the downloaded user data from key 101 to the secured site.

Figure 9:
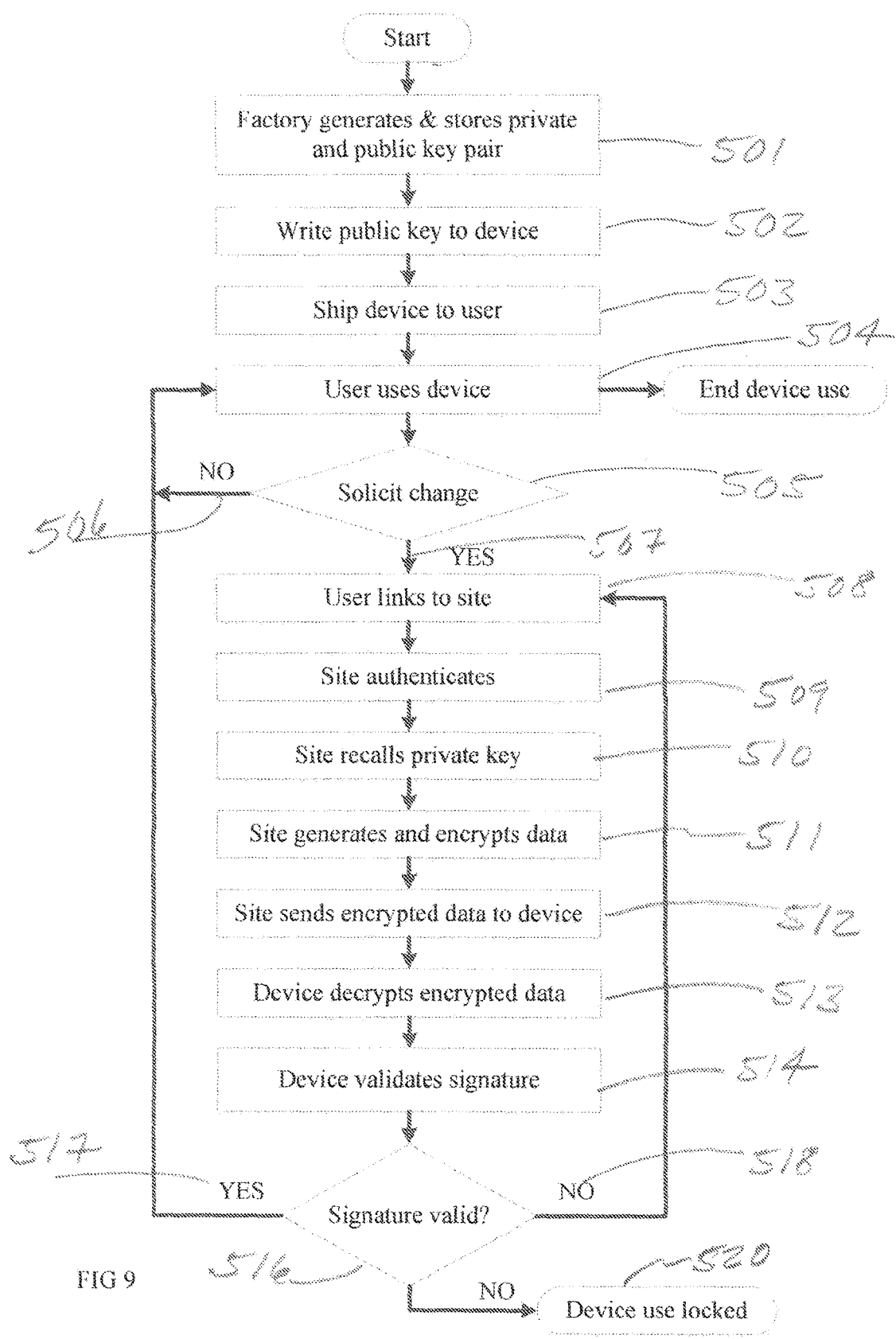
FIG. 9 is a flowchart illustrating methods, in accordance with some embodiments.

Referring to FIG. 9, a flowchart illustrating operation of the system is provided, according to various embodiments. A method can begin with factory generating and storing a private and public key pair (step 501). The next step is write public key into device (step 502) and ship device to user (step 503). After receiving device; user uses device (step 504). Next is a decision in which user or factory solicits change to device (step 505). If no (506), use of the device continues looping back to user uses device (step 505). If yes (507), the next step is user links to site (step 508), followed by site authenticates device via device keys (step 509). In one example, site is located at factory. In another example, site is located at distributor and private and public key pair has been transferred to distributor. Still another example; the site is located at factory and one or more sites are located at one or more distributors which have access to the private and public key pair.

After site authenticates device via device keys (step 509), site recalls private key (step 510). Site generates data for the change and then site encrypts data with private key (step 511). Site sends encrypted data to device (step 513). Upon receipt of the encrypted data, device decrypts data with its public key and validates data digital signature (step 514). Next is a decision, is signature valid? (step 516). If yes (step 517) user can incorporate data into device then user uses device (step 504). If no (step 518), then loop back to user links to site (step 508). Alternatively, if no (step 518), then the device use is locked (step 520). The device maybe locked (step 520) immediately for no in decision, is signature valid? (step 516). However, the device maybe locked (step 520) after a specified numbers of loop back to user links to site (step 508) and receiving no in decision, is signature valid? (step 516).

Figure 10:
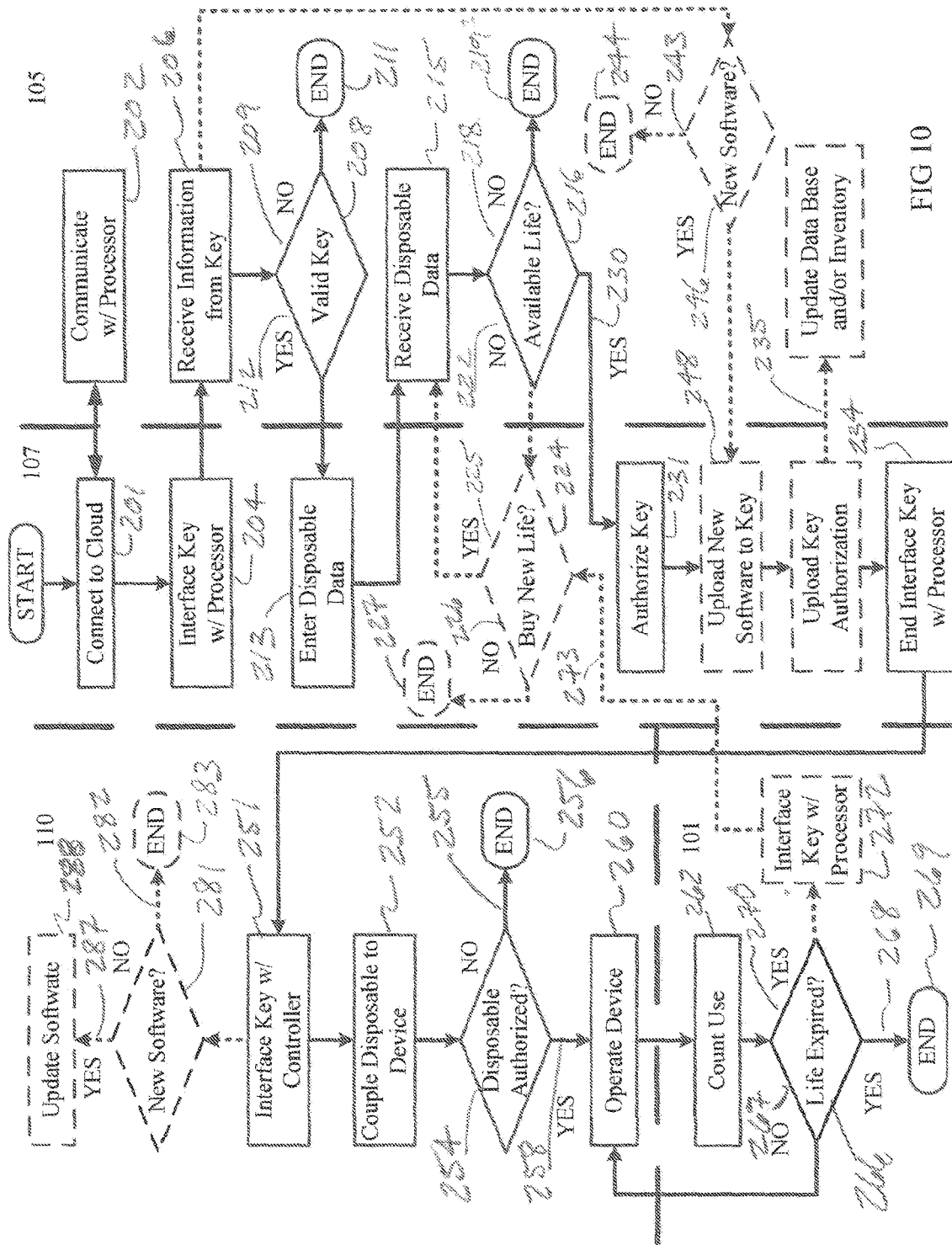
FIG. 10 is a flowchart illustrating methods, in accordance with some embodiments.

Now with reference to FIG. 10, a flowchart illustrating operation of a system is provided, according to various embodiments. FIG. 10 is divided into three sections and each section is marked at the top of the figure with the following: 105 which is the domain of cloud 105; 107 which is the domain of processor 107; and 110 which is the domain of controller 110. Each of the operations and/or processes which are indicated on the flowchart will reside in one of the three sections or domains which are one of 101, 107, or 110. For example, if an operation is in the section under the heading of 105, this operation is being performed in cloud 105. In another example, if an operation is in the section under the heading of 107, this operation is being performed by processor 107. Still another example, if an operation is set in the section under heading 110, this operation is being performed by controller 110.

In the first step, processor 107 connects to a secured site located in cloud 105 (step 201). The secured site in cloud 105 communicates with processor 107 (step 202). Step 201 and step 202 create interface 106. Key 101 is interfaced with processor 107 (step 204). The secured site receives data from key 101 (step 206). The secured site determines if key 101 is valid (step 208). If key 101 is valid then YES (step 212). If key 101 is not valid then NO (step 209) and process ends (step 211). If process ends (step 211), the secured site can send a message to processor 107 communicating status of key 101, as well as, presenting possible remedies to revalidate key 101.

If YES (step 212), then data from component 115 is entered into processor 107. The data from component 115 may include serial number, user ID, password, and combinations thereof and the like. In addition, other data such as, for example, device 114 serial number, application ID, device location and combinations thereof and the like, maybe entered. The data from component 115 can be entered via a keyboard. In some embodiments, the data from component 115 can be entered by scanning a bar code. In some embodiments, the data from component 115 can be entered via a RFID located in the device which can be read by key 101 or processor 107.

The secured site, as described herein and which is located in cloud 105 receives the data from component 115 from processor 107 (step 215). The secured site determines if component 115 is valid (step 216). If component 115 is valid then YES (step 230). If component 115 is not valid then NO (step 218) and process ends (step 219). If process ends (step 219), the secured site can send a message to processor 107 communicating status of component 115, as well as, presenting possible remedies to revalidate component 115. Optionally, if component. 115 is not valid then NO (step 222), the secured site offers the purchase of additional component lifetime (step 224). If YES (step 225), additional component lifetime is added and this new component data is received (step 215) by secured site. If NO (step 226) and process ends (step 227). If process ends (step 227), the secured site can send a message to processor 107 communicating status of component 115.

If component 115 is valid then YES (step 230). The secured site provides authorization codes (step 231) for component 115. The authorization codes are downloaded to key 101 (step 231). The data and/or information related to the component 115, which has been authorized is updated in the database (step 235) of secured site. The interface between key 101 and cloud 105 ends or is severed (step 234).

Key 101 is then interlaced to controller 110 (step 251). Component 115 is coupled to device 114, which is in communication with controller 110 (step 252). Key 101 determines if component 115 is able to be authorized (step 254). If NO (step 255), and process ends (step 256). If process ends (step 256), key 101 can send a message to processor 107 communicating status of component 115, as well as, presenting a reason for failure, for example, mismatch of component 115 serial numbers. In some embodiments, key 101 communicates with EEPROM on component 115 to determine if component 115 is able to be authorized (step 254). If YES (step 258) then key 101 authorizes component 115 and device 114 can be operated (step 262). In some embodiments, key 101 sends authorization codes to EPPROM in component 115 to enable authorization of component 115.

In some embodiments, key 101 counts the use of component 115 (step 262). For example, key 101 can be configured to count each run that component 115 has been used. In an example, key 101 can be configured to count each treatment that component 115 has performed. In some embodiments, a finite lifetime of component 115 can be downloaded to key 101. For example, a finite lifetime of component 115 is a predetermined number of treatments performed and after the predetermined number treatments performed is reached, as counted on key 101, the finite lifetime of component 115 expires. In some embodiments, when the finite lifetime of component 115 expires, component 115 is no longer operable. In some embodiments, when the finite lifetime of component 115 expires, device 114 cannot operate when coupled to component 115 with an expired lifetime. Key 101 determines if finite lifetime of component 115 is expired (step 266). If NO (step 267), then device 114 can continue to operate (step 260). If Yes (step 268), then process ends (step 269) and device 114 can no longer operate.

Optionally, if YES (step 270), then additional lifetime can be added to component 115. If YES (step 270), then the interface between key 101 and controller 110 is ended or severed (step 272). Key 101 is then interfaced with processor 107 (step 273). Processor 107 is interfaced with cloud 105 and the secured site offers the purchase of additional component lifetime (step 224). If YES (step 225), additional component 115 lifetime is added and this new component data is received (step 215) by secured site and the process continues from this step, as previously described.

In some embodiments, after secured site receives data from key 101 (step 206), secured site determines if a new software rev is available for controller 110 (step 242). If NO (step 243), then this portion of the process ends (step 244). If YES (step 246), then new software rev is downloaded to key (step 248) before the interface between key 101 and cloud 105 ends or is severed (step 234).

In some embodiments, after secured site receives data from component 115 (step 215), secured site determines if a new software rev is available for device 114 (step 242). If NO (step 243), then this portion of the process ends (step 244), if YES (step 246), then new software rev is downloaded to key (step 248) before the interface between key 101 and cloud 105 ends or is severed (step 234).

In some embodiments, after key 101 is interfaced to controller 110 (step 251), controller 110 determines if key 101 contains a new software rev (step 281). If NO (step 282), then this portion of the process ends (step 283). If NO (step 282), controller 110 can communicate that software is up to date. If YES (step 287), then controller 110 software is updated from key 101 (step 288). In some embodiments, controller 110 determines if key contains new software rev for device 114 (step 281). If NO (step 282), then this portion of the process ends (step 283). If NO (step 282), controller 110 can communicate that software is up to date. If YES (step 287), then controller 110 updates device 114 software from key 101 (step 288).

Figure 11:
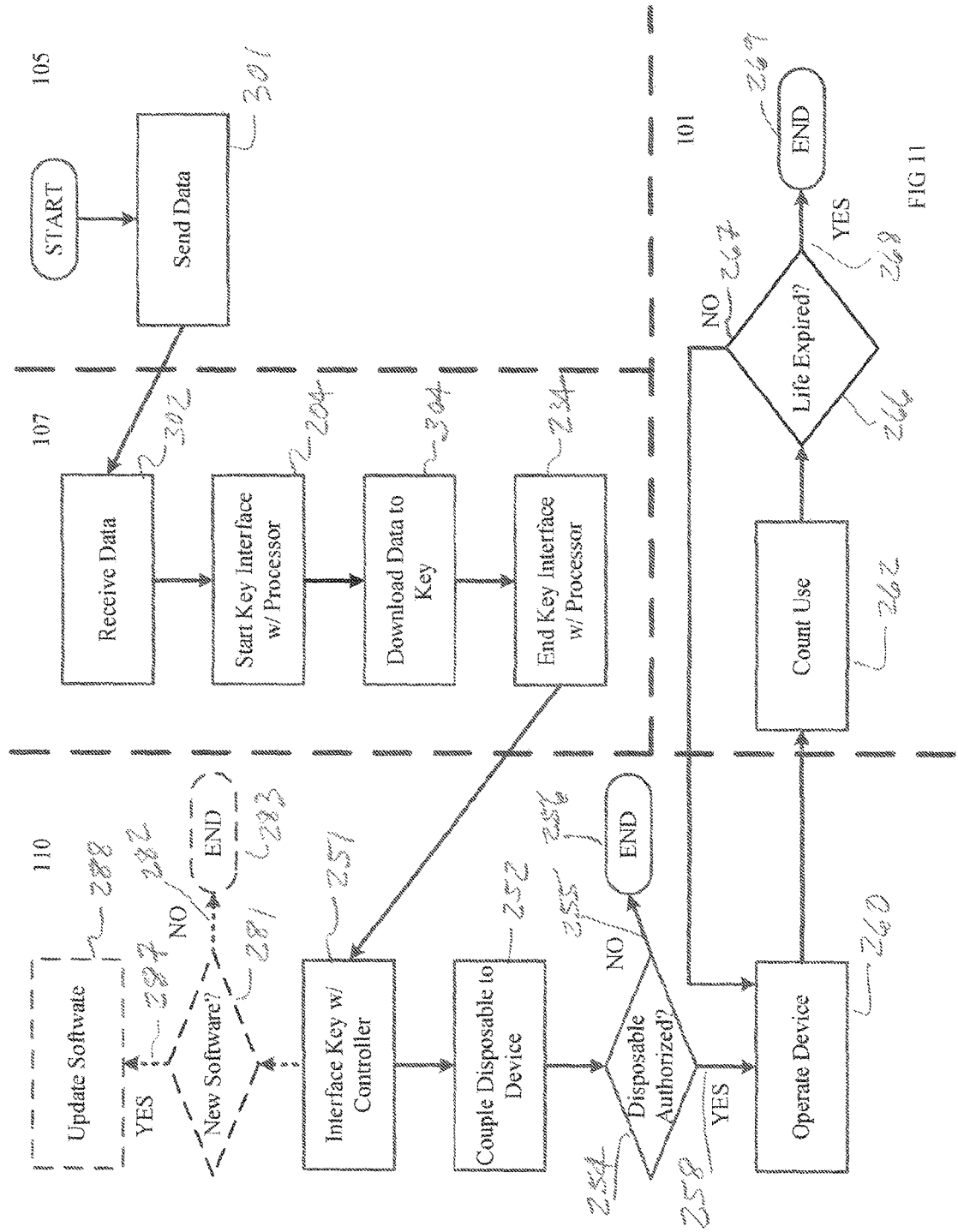
FIG. 11 is a flowchart illustrating methods, in accordance with some embodiments.

Moving to FIG. 11, a flowchart illustrating operation of system 100 is provided according to various embodiments. As illustrated in FIG. 10, FIG. 11 is also divided into three sections and each section is marked at the top of the figure with the following: 105 which is the domain of cloud 105; 107 which is the domain of processor 107; and 110 which is the domain of controller 110.

In the first step, data is sent from cloud 105 to processor 107 (step 301). This step can be wireless, using a radio system, such as a GSM system or other cellular based system to which processor 107 can be in communication with. This step can be as simple as sending an email with an attachment to processor 107. In some embodiments, this step can employ text message and the delivery of data through cloud 105 via such a text system. The next step is the data is received by processor 107 (step 302).

Key 101 is interfaced with processor 107 (step 204). In some embodiments, processor 107 comprises a port which is a USB interface to which key 101 is configured to couple to. In some embodiments, processor 107 comprises a port which communicates wirelessly with key 101. In some embodiments, the port should be configured to communicate with key 101 and allow key 101 to couple to processor 107. The data, which originated in cloud 301, is downloaded to key 101 (step 304).

In some embodiments, processor 107 determines if key 101 is valid. If key 101 is valid then the data is downloaded, if key 101 is not valid then process ends. If process ends, a message can be transmitted by processor 107 communicating status of key 101, as well as, presenting possible remedies to revalidate key 101. In some embodiments, if process ends, processor 107 can send a message to cloud 105 to update a database of key identification and validation information. After the data is downloaded to key 101, the interface between key 101 and processor 107 is severed.

Key 101 is then interfaced to controller 110 (step 251). Component 115 is coupled to device 114, which is in communication with controller 110 (step 252). Key 101 determines if component 115 is able to be authorized (step 254). If NO (step 255), and process ends (step 256). If process ends (step 256), key 101 can send a message to processor 107 communicating status of component 115, as well as, presenting reason for failure, for example, mismatch of component 115 serial numbers. In some embodiments, key 101 communicates with EEPROM on component 115 to determine if component 115 is able to be authorized (step 254). If YES (step 258) then key 101 authorizes component 115 and device 114 can be operated (step 262). In some embodiments, key 101 sends authorization codes to EPPROM in component 115 to enable authorization of component 115.

In some embodiments, key 101 counts the use of component 115, as illustrated in FIG. 11 and as described herein. In some embodiments, after secured site receives data from key 101, secured site determines if a new software rev is available for controller, as illustrated in FIG. 11 and as described herein. In some embodiments, after secured site receives data from component 115, secured site determines if a new software rev is available for device 114, as illustrated in FIG. 11 and as described herein. In some embodiments, after key 101 is interfaced to controller 110, controller 110 determines if key 101 contains a new software rev, as illustrated in FIG. 11 and as described herein.

Figure 12:
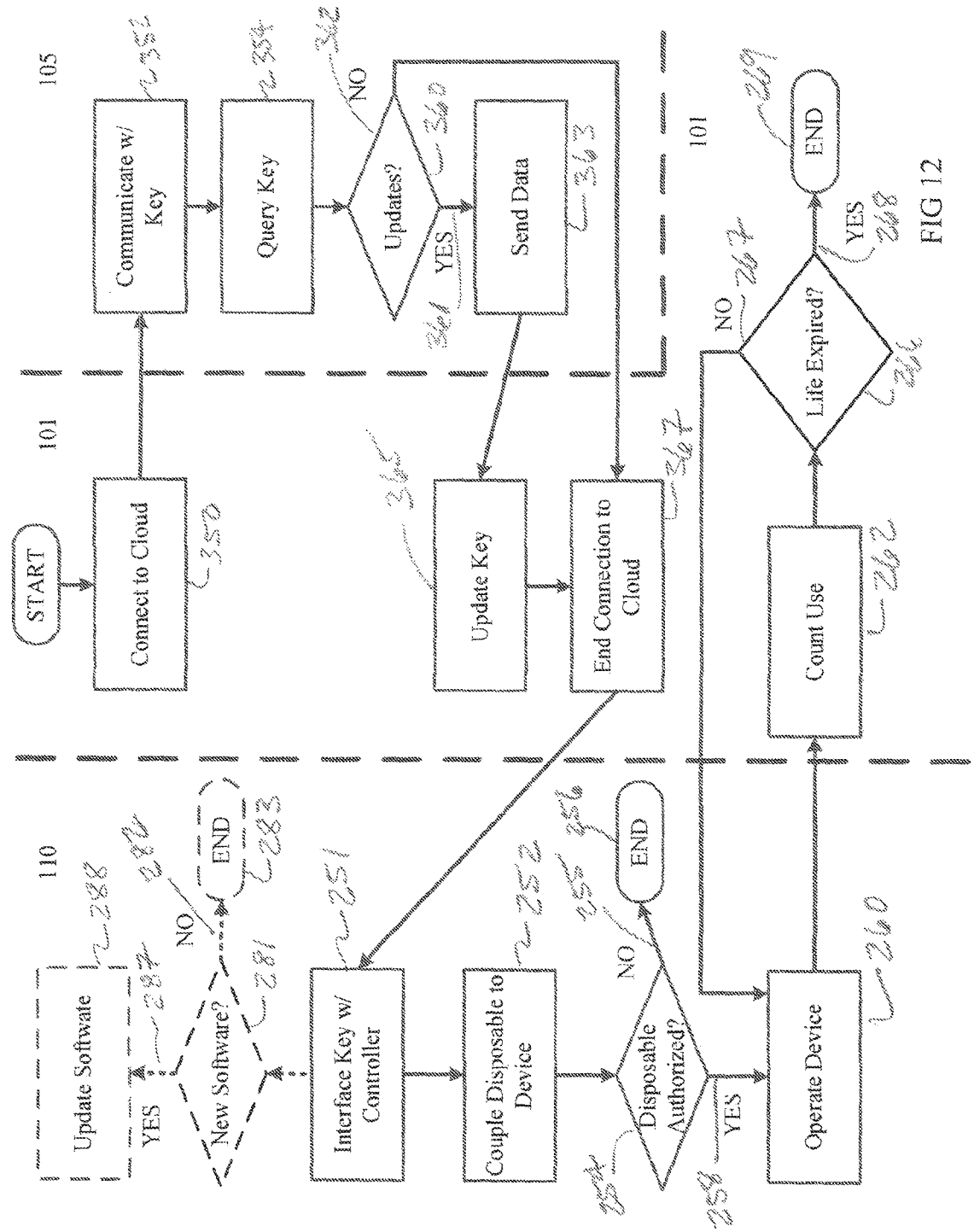
FIG. 12 is a flowchart illustrating methods, in accordance with some embodiments.

Turning to FIG. 12, a flowchart illustrating operation of system 100 is provided according to various embodiments. FIG. 12 is divided into three sections and each section is marked at the top of the figure with the following: 105 which is the domain of cloud 105; 101 which is the domain of key 101; and 110 which is the domain of controller 110.

As described in a similar fashion for the flowcharts illustrated in FIG. 10 and FIG. 11, key 101 connects to cloud 105 (step 350). Cloud 105 communicates with key 101 (step 352), which can be one way or two way communication. Cloud 105 query key 101 (step 354). Decision "any updates?" (step 361). If YES (step 361) cloud collects and sends updates and any other data to key (step 363). Then the key 101 is updated (step 365) and key 101 ends connection to cloud 105 (step 367). If NO (step 362) then key 101 ends connection to cloud 105 (step 367).

In some embodiments, key 101 counts the use of component 115, as illustrated in FIG. 12 and as described herein. In some embodiments, after secured site receives data from key 101, secured site determines if a new software rev is available for controller, as illustrated in FIG. 12 and as described herein. In some embodiments, after secured site receives data from component 115, secured site determines if a new software rev is available for device 114, as illustrated in FIG. 12 and as described herein.

In some embodiments, after key 101 is interfaced to controller 110, controller 110 determines if key 101 contains a new software rev, as illustrated in FIG. 12 and as described herein.

As used herein, the terms "comprise", "comprises", "comprising", "having", "including", "includes" or any variation thereof, are intended to reference a non-exclusive inclusion, such that a process, method, device, system, composition or apparatus that comprises a list of elements does not include only those elements recited, but may also include other elements not expressly listed or inherent to such process, method, device, system, composition or apparatus.

As used herein, the phrase "at least one of A, B, and C" can be construed to mean a logical (A or B or C), using a non-exclusive logical "or," however, can be contrasted to mean (A, B, and C). In addition, can be construed to mean (A and B) or (A and C) or (B and C). As used herein, the phrase "A, B and/or C" should be construed to mean (A, B, and C) or alternatively (A, or B or C), using a non-exclusive logical "or."

It should be understood that steps within a method may be executed in different order without altering the principles of the present disclosure. The some embodiments may be described herein in terms of various functional components and processing steps. It should be appreciated that such components and steps may be realized by any number of hardware components configured to perform the specified functions.

The present invention has been described above with reference to various exemplary embodiments and examples, which are not intended to be limiting in describing the full scope of systems and methods of this invention. However, those skilled in the art will recognize that equivalent changes, modifications and variations of the embodiments, materials, systems, and methods may be made within the scope of the present invention, with substantially similar results, and are intended to be included within the scope of the present invention, as set forth in the following claims.

The invention claimed is:

1. A method for using a component coupled to a medical device, the method comprising:
   detaching a first component from a medical device that is in communication with a device controller;

interfacing a communication key with a computer cloud via a networked computing device while the communication key is not interfaced with the device controller;

downloading, via the networked computing device, encrypted authorization codes from the cloud onto the communication key;

severing communication between the computer cloud and the communication key by physically disconnecting the communication key from the networked computing device while the communication key is not interfaced with the device controller;

interfacing the communication key with the device controller that is in communication with the medical device after communication between the computer cloud and the communication key has been severed;

physically coupling a second component to the medical device in place of the first component;

downloading, while communication between the computer cloud and the communication key is severed, the encrypted authorization codes from the communication key to at least one of the medical device and the second component; and initiating the second component for use when coupled to the medical device.

2. The method according to claim 1, the method further comprising determining if the component is valid using at least one of the encrypted authorization codes.

3. The method according to claim 1, the method further comprising:
operating the medical device and the component;
counting a number of treatments performed by the component during the operating the medical device and the component;
providing a limit of the number of treatments performed by the component during the operating the medical device and the component; and
disabling the component upon reaching a limit of the number of treatments performed by the component during the operating the medical device and the component.

4. The method according to claim 1, wherein the encrypted authorization codes enable operation of the component.

5. The method according to claim 1, the method further comprising:
reviewing a current version of software on the controller:
determining if a software update is available on the communication key; and
downloading the software update from the communication key to the device controller and updating the current version of software with the software update.

6. A treatment system comprising:
a secured key comprising encrypted protected memory configured to store at least a first authorization code;
a secured site located on a computing cloud and configured to securely communicate authorization codes to the secured key;
an interface configured for secured communication between the secured site and the secured key;
a treatment device;
a device controller in communication with and configured to control the treatment device, the device controller comprising a wired communication port configured for communication with the secured key; and
a component physically coupled to the treatment device and in communication with the secured key, wherein the component is associated with, and enabled to perform a treatment by, the first authorization code, and the component is configured to be detached from the treatment device to facilitate replacement with a new component associated with a second authorization code.

7. The treatment system according to claim 6, further comprising a processor configured to communicate with the secured site and comprising a second wired communication port configured for communication with the secured key.

8. The treatment system according to claim 6, wherein the component further comprises an EEPROM, and wherein the component is configured to receive the first authorization code from the secured key and communicate with the EEPROM to determine if the component is valid based on an authorization protocol and using the first authorization code.

9. The treatment system according to claim 6, further comprising:
a treatment counter embedded into the secured key and in communication with the component; and
an expiration function configured to execute after a predetermined number of treatments as clocked by the treatment counter and configured to disable operation of the component upon completion of the predetermined number of treatments.

10. The treatment system according to claim 6, further comprising a software update configured to be delivered from the secured site to the secured key and further configured to be uploaded from the secured key to the device controller and configured to update a software rev on running the device controller.

11. The treatment system according to claim 6, further comprising a firewall configured to automatically operate upon operation of the component and configured to prevent any communication to the device controller from the computer cloud.

12. A method of enabling a treatment device, the method comprising:
detaching a first component treatment module from a treatment device, wherein the first component treatment module comprises a first ultrasound transducer module and a first memory;
downloading an authorization code from a cloud computing network onto a secured electronic key;
downloading data corresponding to a new treatment method for the treatment device from the cloud computing network onto the secured electronic key;
interfacing the secured electronic key with a second component treatment module that is physically coupled to the treatment device in place of the first component treatment module, wherein the second component treatment module comprises a second ultrasound transducer module and a second memory, and is configured to perform the new treatment method;
initiating communication between the secured electronic key and the second memory of the second component treatment module;
determining if the second component treatment module is enabled to be authorized by the secured electronic key;
downloading the authorization code from the secured electronic key to the second memory of the second component treatment module;
authorizing the second component treatment module with the authorization code; and
in response to authorizing the second component treatment module, enabling operation of the treatment device physically coupled to the second component treatment module to perform the new treatment method.

13. The method according to claim 12, the method further comprising the steps of:
determining that the second component treatment module is not enabled to be authorized by the secured electronic key;
in response to determining that the second component treatment module is not enabled to be authorized by the secured electronic key, disabling the second component treatment module; and
in response to disabling the second component treatment module, preventing operation of the treatment device physically coupled to the second component treatment module.

14. The method according to claim 12, the method further comprising:
operating the treatment device physically coupled to the second component treatment module to perform the new treatment; and
counting on the secured electronic key a number of treatments performed by the second component treatment module during the operating the treatment device physically coupled to the second component treatment module.

15. The method according to claim 14, the method further comprising:
providing on the secured electronic key a limit of the number of treatments performed by the second component treatment module during the operating the treatment device physically coupled to the second component treatment module; and
disabling the second component treatment module upon reaching the limit of the number of treatments performed by the second component treatment module during the operating the treatment device physically coupled to the second component treatment module.

16. The method according to claim 12, the method further comprising establishing a communication interface between the secured electronic key and the cloud computing network before the step of downloading the authorization code from the cloud computing network onto the secured electronic key.

17. The method according to claim 16, the method further comprising severing the communication interface between the secured electronic key and the cloud computing network after the step of downloading the authorization code from the cloud computing network onto the secured electronic key.

18. The method according to claim 12, the method further comprising the steps of:
downloading a software update from the cloud computing network onto the secured electronic key;
notifying the treatment device of the software update upon the step of the initiating communication between the secured electronic key and the second component treatment module;
downloading the software update from the secured electronic key to the treatment device; and
initiating the software update on the treatment device.

19. The method according to claim 12, the method further comprising preventing the secured electronic key from interfacing with the cloud computing network upon the step of the initiating communication between the secured electronic key and the second component treatment module.

20. The method according to claim 12, the method further comprising
collecting information from the treatment device onto the secured electronic key; and
uploading the information from the secured key to the cloud computing network, wherein the information comprises at least one of treatment logs, diagnostic information, and treatment device usage.

* * * * *

UNITED STATES PATENT AND TRADEMARK OFFICE
CERTIFICATE OF CORRECTION

PATENT NO. : 10,148,439 B2
APPLICATION NO. : 14/777054
DATED : December 4, 2018
INVENTOR(S) : Peter G. Barthe Page 1 of 1

It is certified that error appears in the above-identified patent and that said Letters Patent is hereby corrected as shown below:

In the Specification

Column 2, Line 65, "to the" should be --to limit the--.

Column 6, Line 2, "Can" should be --can--.

Column 6, Line 34, "It" should be --In--.

Column 10, Line 3, "interfacing communication" should be --interfacing a communication--.

Column 10, Line 44, "seemed" should be --secured--.

Column 11, Line 22, "cot" should be --treatment--.

Column 11, Line 60, "RE" should be --RF--.

Column 13, Line 62, "interlaced" should be --interfaced--.

Signed and Sealed this
Fifth Day of February, 2019

Andrei Iancu
*Director of the United States Patent and Trademark Office*